United States Patent
Dehghan Marvast et al.

(10) Patent No.: US 11,135,447 B2
(45) Date of Patent: Oct. 5, 2021

(54) GUIDANCE FOR LUNG CANCER RADIATION

(71) Applicant: KONINKLIJKE PHILIPS N.V., Eindhoven (NL)

(72) Inventors: Ehsan Dehghan Marvast, New York, NY (US); Davide Fontanarosa, Neerpelt (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 386 days.

(21) Appl. No.: 15/743,005

(22) PCT Filed: Jul. 15, 2016

(86) PCT No.: PCT/EP2016/066912
§ 371 (c)(1),
(2) Date: Jan. 9, 2018

(87) PCT Pub. No.: WO2017/013019
PCT Pub. Date: Jan. 26, 2017

(65) Prior Publication Data
US 2018/0214713 A1    Aug. 2, 2018

Related U.S. Application Data

(60) Provisional application No. 62/193,617, filed on Jul. 17, 2015.

(51) Int. Cl.
*A61N 5/10* (2006.01)
*A61B 8/08* (2006.01)

(52) U.S. Cl.
CPC .......... *A61N 5/1037* (2013.01); *A61B 8/085* (2013.01); *A61N 5/1049* (2013.01);
(Continued)

(58) Field of Classification Search
CPC .......... A61N 5/1037; A61B 6/06; A61B 6/40; A61B 6/482; A61B 8/00; A61B 8/13;
(Continued)

(56) References Cited

U.S. PATENT DOCUMENTS 4,899,393 A * 2/1990 Morishita ............. G06T 3/4061
382/130
5,447,154 A * 9/1995 Cinquin .................. A61B 6/12
600/429
(Continued)

FOREIGN PATENT DOCUMENTS

JP    2008154861 A    7/2008
WO   2006/057911     6/2006
(Continued)

OTHER PUBLICATIONS

Shen, et al., "Validation of target volume and position in respiratory gated CT planning and treatment", Med. Phys. 30 (12), Dec. 2003.
(Continued)

*Primary Examiner* — David P Porta
*Assistant Examiner* — Djura Malevic (57) ABSTRACT

An ultrasound device (18) is arranged to acquire an ultrasound image (19) of a thoracic diaphragm. A current location (24) of a tumor is determined using the ultrasound image (19) of the thoracic diaphragm and a predetermined relationship (14) assigning tumor locations to a set of simulation phase ultrasound images of the thoracic diaphragm in different geometries, or using a predetermined relationship (114) assigning tumor locations to a set of meshes representing the thoracic diaphragm in different geometries. The tumor may, for example, be a lung tumor.

19 Claims, 7 Drawing Sheets

(52) U.S. Cl.
CPC ............ *A61N 5/1067* (2013.01); *A61B 8/483* (2013.01); *A61B 8/5246* (2013.01); *A61B 8/5261* (2013.01); *A61N 2005/1058* (2013.01)

(58) Field of Classification Search
CPC ... A61B 8/5261; A61B 8/4416; A61B 8/4477; A61B 8/4483; A61B 8/5238; G01N 23/044; G01N 23/20008; G01N 2223/316; G02B 27/0927; G02B 27/0983; G02B 5/10; G21K 1/02; G21K 1/067; G21K 2201/064

See application file for complete search history.

(56) References Cited

U.S. PATENT DOCUMENTS

| | | | | |
|---|---|---|---|---|
| 5,672,877 | A * | 9/1997 | Liebig | A61B 6/5235 250/363.04 |
| 5,846,513 | A * | 12/1998 | Carroll | A61B 6/4057 424/1.11 |
| 6,325,758 | B1 * | 12/2001 | Carol | A61N 5/1049 128/916 |
| 6,560,354 | B1 * | 5/2003 | Maurer, Jr. | G06T 7/33 128/922 |
| 6,961,405 | B2 * | 11/2005 | Scherch | A61B 8/08 378/65 |
| 8,111,892 | B2 * | 2/2012 | Hyun | A61B 6/032 382/128 |
| 8,942,342 | B2 | 1/2015 | Abenaim | |
| 9,108,048 | B2 * | 8/2015 | Maurer, Jr. | A61B 6/5247 |
| 9,873,003 | B2 * | 1/2018 | Tsunoo | A61N 5/1049 |
| 9,950,194 | B2 * | 4/2018 | Bouchet | A61N 5/1049 |
| 10,368,809 | B2 * | 8/2019 | Kim | A61N 7/02 |
| 2004/0034301 | A1 * | 2/2004 | Falco | A61B 8/08 600/427 |
| 2005/0180544 | A1 * | 8/2005 | Sauer | A61N 5/1049 378/195 |
| 2006/0074292 | A1 * | 4/2006 | Thomson | A61B 6/032 600/411 |
| 2007/0003123 | A1 * | 1/2007 | Fu | A61N 5/1049 382/131 |
| 2007/0015991 | A1 * | 1/2007 | Fu | A61B 8/08 600/407 |
| 2007/0038058 | A1 * | 2/2007 | West | A61N 5/1049 600/407 |
| 2007/0041639 | A1 * | 2/2007 | Von Berg | G06T 7/0012 382/173 |
| 2007/0276214 | A1 * | 11/2007 | Dachille | G06T 7/0012 600/407 |
| 2007/0286342 | A1 * | 12/2007 | Fuller | A61N 5/103 378/65 |
| 2008/0008369 | A1 * | 1/2008 | Koptenko | G06K 9/4604 382/128 |
| 2008/0119725 | A1 * | 5/2008 | Lloyd | A61B 90/36 600/424 |
| 2008/0123927 | A1 * | 5/2008 | Miga | G06T 7/344 382/131 |
| 2008/0177279 | A1 * | 7/2008 | Sumanaweera | A61N 5/1049 606/130 |
| 2008/0187095 | A1 * | 8/2008 | Boone | A61B 8/0825 378/37 |
| 2008/0219540 | A1 * | 9/2008 | Ter Mors | G06T 15/08 382/132 |
| 2009/0088897 | A1 * | 4/2009 | Zhao | G06K 9/3216 700/250 |
| 2009/0275830 | A1 | 11/2009 | Falco | |
| 2009/0304252 | A1 * | 12/2009 | Hyun | A61B 5/04284 382/131 |
| 2010/0289813 | A1 * | 11/2010 | Nobe | A61B 6/032 345/597 |
| 2011/0028844 | A1 * | 2/2011 | Hyun | A61B 5/0035 600/443 |
| 2011/0103666 | A1 * | 5/2011 | Ohishi | A61B 6/463 382/131 |
| 2011/0135177 | A1 * | 6/2011 | Ohishi | A61B 6/481 382/130 |
| 2011/0150312 | A1 * | 6/2011 | Takanami | G06T 17/20 382/131 |
| 2012/0004553 | A1 | 1/2012 | Kanayama | |
| 2012/0014559 | A1 * | 1/2012 | Suehling | G06K 9/6207 382/103 |
| 2012/0027261 | A1 * | 2/2012 | Frank | A61B 6/4441 382/103 |
| 2012/0035462 | A1 * | 2/2012 | Maurer, Jr. | A61B 6/5247 600/411 |
| 2012/0046545 | A1 * | 2/2012 | Averbuch | A61B 5/06 600/427 |
| 2012/0051664 | A1 * | 3/2012 | Gopalakrishnan | G06T 11/005 382/294 |
| 2012/0071757 | A1 * | 3/2012 | Salcudean | A61B 8/0841 600/439 |
| 2012/0082351 | A1 * | 4/2012 | Higgins | A61B 1/00147 382/128 |
| 2012/0250966 | A1 * | 10/2012 | Fujisawa | G06T 7/0016 382/131 |
| 2012/0253170 | A1 * | 10/2012 | Kim | A61B 34/10 600/410 |
| 2014/0046172 | A1 * | 2/2014 | Kim | A61B 5/7275 600/411 |
| 2014/0126797 | A1 | 5/2014 | Kaus | |
| 2014/0275966 | A1 * | 9/2014 | Schwartz | A61B 8/4236 600/411 |
| 2014/0316247 | A1 * | 10/2014 | Hwang | A61B 8/08 600/411 |
| 2015/0314138 | A1 * | 11/2015 | Maurer | A61B 6/5247 600/411 |

FOREIGN PATENT DOCUMENTS

| | | |
|---|---|---|
| WO | 2012/019162 | 2/2012 |
| WO | 2012/142031 | 10/2012 |
| WO | 2013028762 | 2/2013 |

OTHER PUBLICATIONS

Spoelstra, et al., "Feasibility of using anatomical surrogates for predicting the positionof lung tumours", Radiotherapy and Oncology, 2012, 102, 287-289.

Cervino, et al., "Tumor motion prediction with the diaphragm as asurrogate: a feasibility study", Phys. Med. Biol. 55 (2010) N221-N229.

Vedam, et al., "Acquiring a four-dimensional computed tomography dataset using an external respiratory signal", Phys. Med. Biol. 48 (2003) 45-62.

John Wong, "Methods to manage respiratory motion in radiation treatment", 2005.

Caskey, et al., "An Open Environment CT-US Fusion for Tissue Segmentation during Interventional Guidance", PLOS One, Nov. 2011, vol. 6, Issue 11.

* cited by examiner

GUIDANCE FOR LUNG CANCER RADIATION

CROSS REFERENCE TO RELATED APPLICATIONS

This application is the U.S. National Phase application under 35 U.S.C. §371 of International Application No. PCT/EP2016/066912, filed Jul. 15, 2016, published as WO 2017/013019 on Jan. 26, 2017, which claims the benefit of U.S. Provisional Patent Application Number 62/193,617 filed Jul. 17, 2015. These applications are hereby incorporated by reference herein.

BACKGROUND

The following relates to targeting radiation towards a tumor.

In radiation therapy (RT), a therapeutic radiation beam is applied to the tumor. To avoid damaging neighboring healthy tissue or organs, the RT is typically planned in advance, using a computed tomography (CT) or magnetic resonance (MR) image of the region of the patient containing the tumor. In one approach, the radiation therapy planning (sometimes called RT "simulation") computes a simulated absorbed radiation dose distribution in the tumor and surrounding tissue, and parameters of the radiation therapy (e.g. beam positions, multi-leaf collimator settings, tomography parameters, or so forth) are adjusted in the simulation to obtain a simulated radiation therapy dose that meets the planning criteria (e.g. obtaining at least a minimum dose in the tumor in combination with keeping the dose in critical healthy organs/tissue below some specified maximum threshold). In RT of a lung tumor or other tumor in the thoracic cavity, respiratory motion is problematic because the lung tumor moves along with a patient's inhalation and exhalation making the tumor difficult to target.

A conventional solution to dealing with the movement of the lung tumor is to plan the RT so as to apply radiation with margins large enough to encompass the tumor throughout the respiratory cycle. Unfortunately, this injects additional radiation dose into surrounding healthy tissue. This can be especially problematic considering the potentially close proximity of other vital organs (e.g. the heart) to the lung tumor.

A variant approach is to design the margin for a particular respiratory phase (e.g. exhalation) and perform respiratory gating using a spirometer or other respiration monitor to determine what phase of breathing a patient is in. In this way, the radiation beam may be shuttered off during parts of the respiratory cycle while the tumor is known to be in a certain position. However, the correlation between respiratory phase and lung tumor position is indirect and may be weak.

SUMMARY

In accordance with one aspect, a tumor detection device comprises an electronic device programmed to receive an ultrasound image and determine a current location of a tumor using the received ultrasound image. In some embodiments the current location of the tumor is determined by: comparing the ultrasound image with a plurality of simulation phase ultrasound images to identify a most similar simulation phase ultrasound image; and determining the current location of the tumor using a predetermined relationship assigning a location of the tumor to each simulation phase ultrasound image of the plurality of simulation phase ultrasound images. In some embodiments the current location of the tumor is determined by: comparing an anatomical feature imaged in the ultrasound image with a plurality of meshes representing the anatomical feature in different locations to identify a most similar mesh; and determining the current location of the tumor using a predetermined relationship assigning a location of the tumor to each mesh of the plurality of meshes. In some embodiments the anatomical feature is a thoracic diaphragm and the tumor is a lung tumor.

In accordance with another aspect, a tumor detection device comprises: an ultrasound device arranged to acquire an ultrasound image of a thoracic diaphragm; and an electronic data processing device programmed to determine a current location of a tumor using the ultrasound image of the thoracic diaphragm and a predetermined relationship assigning tumor locations to a set of simulation phase ultrasound images of the thoracic diaphragm in different geometries or to a set of meshes representing the thoracic diaphragm in different geometries.

In accordance with another aspect, a tumor detection method comprises acquiring an ultrasound image of a thoracic diaphragm of a patient and determining a current location of a tumor of the patient using the acquired ultrasound image and a tumor-locating relationship. The determining does not include detecting the tumor in the acquired ultrasound image. The tumor may, for example, be a lung tumor.

One advantage resides in, during radiation therapy of a lung tumor, a lesser amount of radiation being delivered to vital organs.

Another advantage resides in improved targeting of a moving tumor during radiation therapy.

Other advantages will become apparent to one of ordinary skill in the art upon reading and understanding this disclosure. It is to be understood that a specific embodiment may attain, none, one, two, more, or all of these advantages.

The invention may take form in various components and arrangements of components, and in various steps and arrangements of steps. The drawings are only for purposes of illustrating the preferred embodiments and are not to be construed as limiting the invention.

DETAILED DESCRIPTION

In approaches disclosed herein, the imaged position of a thoracic diaphragm is leveraged to determine and track the position of a lung tumor during radiation therapy (RT). It is recognized herein that the position of the thoracic diaphragm provides a good surrogate for tumor position. Respiration is driven by the thoracic diaphragm, which contracts and moves in the inferior direction during inhalation to cause the lungs to expand—motion of the lung tumor is caused by, and therefore generally correlates with, this motion of the diaphragm. Advantageously, the diaphragm position may be monitored by ultrasound imaging. By contrast, ultrasound imaging to directly measure and track the position of a lung tumor during RT is not practical because of air in the lungs.

To make use of the foregoing approach, it is disclosed to match information collected during a simulation or planning phase with diaphragm position imaged by ultrasound during a treatment phase to obtain a position of a lung tumor.

Figure 1:
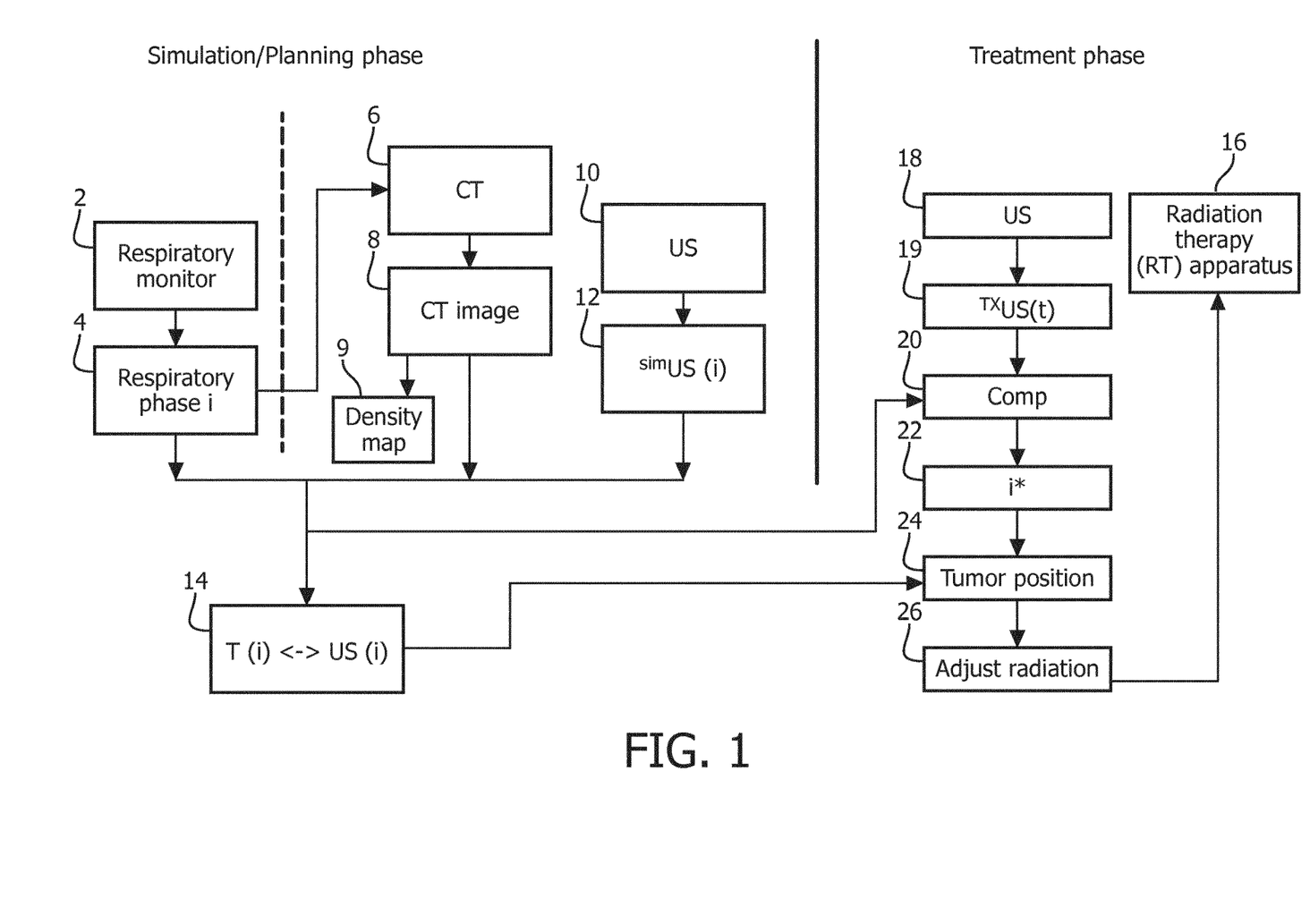
FIG. 1 diagrammatically shows a first preferred embodiment which includes ultrasound images taken during a simulation phase.

With reference to FIG. 1, during a simulation or planning phase, lung tumor position is correlated with ultrasound images of the diaphragm. In some embodiments, a respiratory monitor 2 monitors respiratory phase 4 so that tumor position over the respiratory cycle is captured; however, in some embodiments it is contemplated to omit the respiratory monitoring. In the illustrative embodiment of FIG. 1, computed tomography (CT) images 8 of a patient may be taken in using a computed tomography (CT) imaging system 6. These CT images for radiation therapy planning are usually three-dimensional images. Moreover, CT images are acquired at various times (sometimes referred to as 4DCT). In a typical 4DCT approach, respiratory gating based on the respiratory phase 4 is employed to assign CT imaging data to different respiratory phase "bins" which are each reconstructed to generate an image of the tumor at a different respiratory phase.

The CT images 8 inform on the position of a lung tumor, and may be used to generate a density map 9 for use in the radiation therapy planning. To produce the density map 9, the CT image 8 may be adjusted for differences in absorption coefficient of the therapeutic radiation used in RT as compared with the x-rays used in CT imaging. More generally, the CT imaging system 6 may be replaced by another imaging modality that provides contrast for both the lung tumor and the thoracic diaphragm. For example, it is contemplated that a magnetic resonance imaging (MRI) system may be used in place of the CT imaging system 6. In this case, the density map may be generated by an approach such as segmenting the MRI image to identify regions of different tissue types (e.g. bone, fat, muscle, air in lungs) and assigning appropriate radiation absorption values for each tissue region.

Also during the simulation phase, ultrasound images of patient are acquired using an ultrasound imaging device or system 10. As previously mentioned, the ultrasound images do not generally provide good contrast for the lung tumor, but the ultrasound images do image the thoracic diaphragm. Accordingly, a geometry of the thoracic diaphragm of the patient is captured in ultrasound images 12 acquired by the ultrasound imaging system 10. As is known in the art, the thoracic diaphragm contracts to expand the lungs during inhalation, and relaxes during exhalation. The detailed motion of the thoracic diaphragm can be complex, and may include aspects of non-rigid shape deformation, translation, rotation, or various combinations thereof for various portions of the thoracic diaphragm. The term "geometry" of the thoracic diaphragm and similar phraseology as used herein encompasses all such movement, rotation, deformation or other geometric change of the thoracic diaphragm.

In general, the ultrasound images 12 may be either two-dimensional or three-dimensional. If two-dimensional ultrasound images 12 are employed, then the orientation of the image should be chosen to capture the principal inferior/superior (inhalation/exhalation) motion of the diaphragm. For example, by positioning the ultrasound probe generally below (i.e. inferior with respect to) the diaphragm (e.g. a subcostal or intercostal oblique probe position), a two-dimensional US image can be obtained in a slanted coronal plane that intersects the generally planar diaphragm muscle sheet so as to effectively capture this motion. Since the ultrasound images 12 will later be compared with ultrasound images acquired during the RT treatment phase, the ultrasound probe should also be positioned so as to not interfere with (e.g. block) the RT beam(s). The subcostal probe position is generally effective to locate the ultrasound probe inferior to the RT beam(s).

The position T(i) of the lung tumor is obtained by manual, semi-automated, or automated segmentation of the CT image 8. This tumor position T(i) is correlated with corresponding ultrasound images US(i) to generate a relationship 14 denoted T(i)-US(i) between location T(i) of the malignant tumor and the ultrasound images US(i) of the thoracic diaphragm acquired during the simulation phase. By the relationship 14, a position of the diaphragm may be correlated with a position of the tumor. To correlate CT information with ultrasound information, many different techniques are possible. One such technique is to measure the CT information and ultrasound information simultaneously. That way, time stamps from the CT information may be matched with time stamps from the ultrasound information to achieve the correlation. In this case, the index i suitably denotes the timestamp. (Note in this embodiment the respiratory monitor 2 is used to perform respiratory gating to generate the 4DCT images). Another such technique is to use the breathing signal 4 to correlate the CT information with the ultrasound information. If this technique is used, the CT information and the ultrasound information do not need to be collected at the same time, and here the index i denotes respiratory phase.

Figure 4:
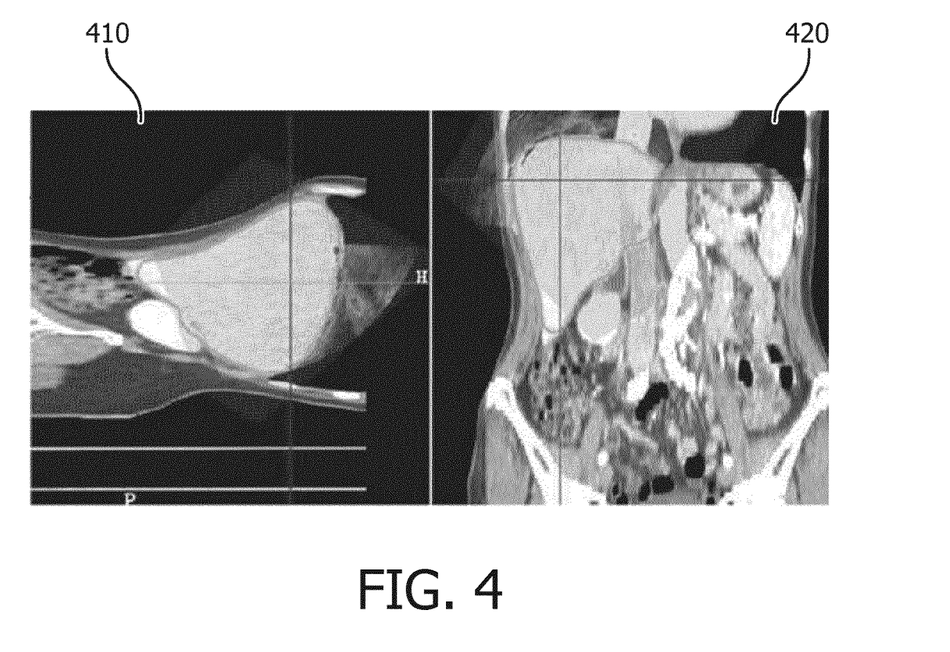
FIG. 4 shows two examples of overlays of an ultrasound volume on a CT volume.

With brief reference to FIG. 4, yet another illustrative technique is to correlate the ultrasound and CT images/volumes with each other based on the position of the diaphragm in the two modalities. As the CT and ultrasound images/volumes are spatially co-registered, for each CT volume in a "4-dimensional" CT (4DCT) series (time is the fourth dimension; and 4DCT will be described below), an ultrasound volume may be found in which the diaphragm positon in the ultrasound volume has the best overlap with the diaphragm position in the CT (see, e.g., FIG. 4). Therefore, for each CT volume $CT_i$ there will be a corresponding ultrasound image/volume $^{sim}US_i$ that is acquired at the similar breathing phase. FIG. 4 shows an overlay of an ultrasound volume on a CT volume in sagittal view 410, and coronal view 420. For example, FIG. 4 shows a good overlap of diaphragm in the two modalities. In this case, the index i is suitably an arbitrary index indicating that the malignant tumor position T(i) was obtained from a CT image for which the diaphragm was in the same position (within some fitting tolerance) as the diaphragm position in the corresponding ultrasound image $^{sim}US(i)$. (Note in this embodiment as well the respiratory monitor 2 is optionally omitted unless needed to perform respiratory gating to generate the 4DCT images).

Figure 3:
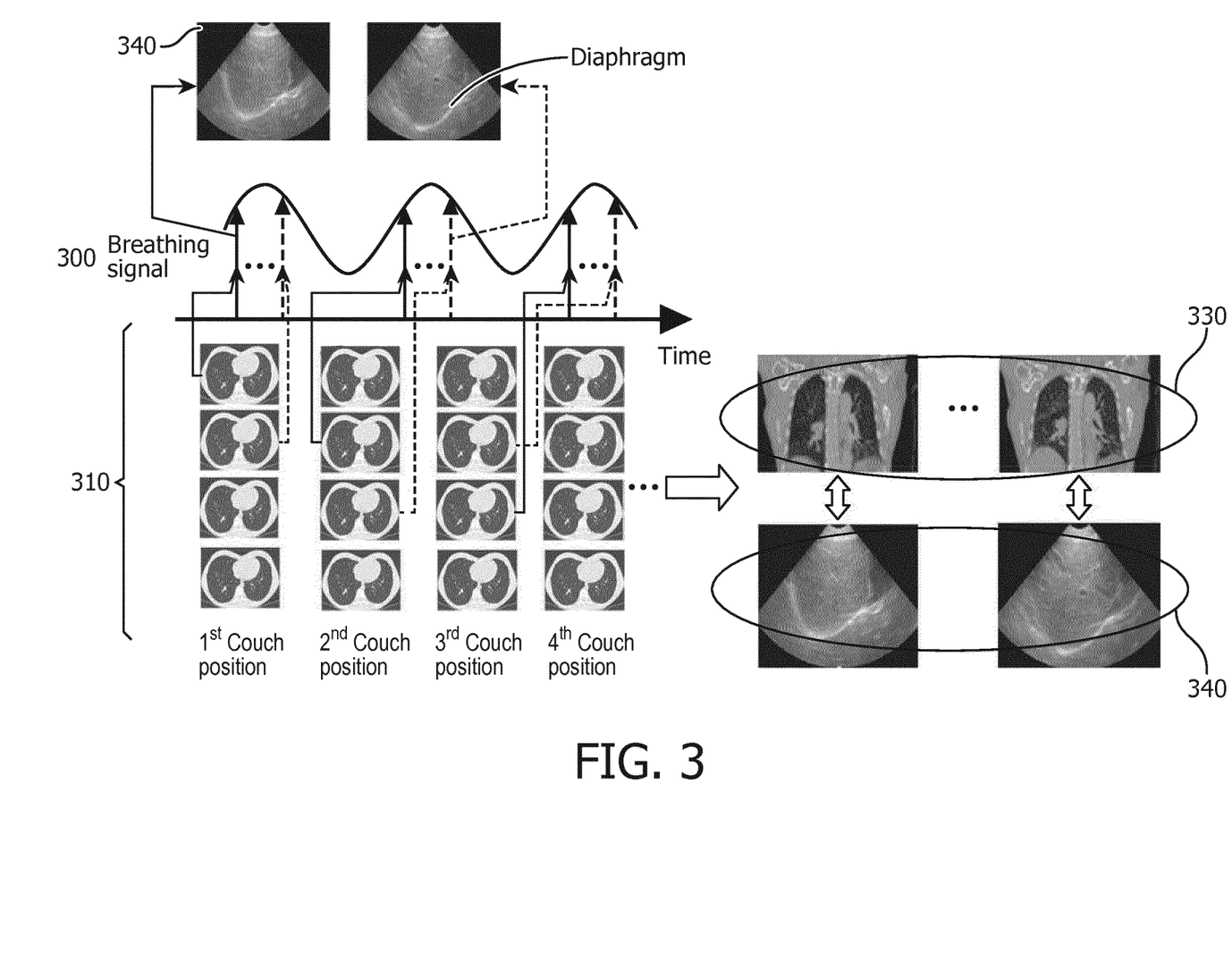
FIG. 3 shows an example of acquiring corresponding ultrasound and CT images/volumes.

With reference to FIG. 3, an illustrative example is described using the approach in which respiratory phase is used to correlate malignant tumor position with ultrasound images (so that in this illustrative example the index i denotes respiratory phase). FIG. 3 shows breathing signal 300. To measure a breathing signal, a spirometer (which is a device for measuring a volume of air moving into and flowing out of the lungs) may be used. Another technique to measure breathing signal is by use of a respiration monitor in the form of an abdominal belt placed on a patient. Yet another technique is to place an optically localized object on a patient and measure the movement of the object. Any of these devices may be used as the respiratory monitor 2 of FIG. 1. As yet another example, CT images, MRI images, or any other kind of suitable images may be used to generate the breathing signal 4 based on cyclic variation of the images over time.

With continuing reference to FIG. 3, CT images of a patient may be taken at different couch positions. One having ordinary skill in the art will understand that, with respect to CT, different couch positions means different axial positions of a patient lying on a couch, e.g. in a supine (face-up) or prone (face-down) position, and moving along a horizontal axis through a gantry of the CT machine 6. Images 310 are examples of images taken at different couch positions.

To elaborate, several CT slices are acquired at each couch position. Each image corresponds to a breathing signal phase/amplitude (e.g. of breathing signal 310). The slices that have similar breathing signal phase/amplitude are binned together and sorted based on their couch position. Finally they are concatenated into a 3D volume corresponding to a breathing signal phase (e.g. images 330). Ultrasound images/volumes can be acquired with a similar breathing signal (e.g. images 340) and then associated with CT volumes (e.g. images 330) in a "4-dimensional" CT (4DCT) series (time is the fourth dimension).

The illustrative ultrasound images 340 were acquired with the ultrasound probe in the subcostal or intercostals position. Notably, in FIG. 3, the high intensity (bright) line on ultrasound images 340 shows the thoracic diaphragm of the patient.

Returning now to FIG. 1, a radiation therapy (RT) plan is developed using information gathered during the simulation phase, such as the density map 9. The RT plan is typically generated by simulating the radiation dose distribution in the patient assuming specified RT parameters such as number/angles of beams (for multi-beam RT), multi-leaf collimator settings, tomography parameters (for tomographic RT, e.g. employing a linac), or so forth. The therapeutic radiation beam may, in general, be of any type used in RT, such as an accelerated beam of electrons, protons, or so forth. As previously mentioned, absorption coefficients of the CT-generated image 8 may be suitably adjusted to account for the type and particle energy of the RT beam(s) in order to produce the density map 9. The RT parameters are adjusted during the simulation phase to optimize the simulated radiation dose distribution in the patient, so as to develop the RT plan. Thereafter, in a treatment phase, which occurs subsequent to the simulation phase, a radiation therapy session is performed in which radiation therapy is delivered in accordance with the RT plan. It is during the treatment phase that therapeutic radiation is delivered to the patient. During the treatment phase, radiation therapy is delivered by a radiation therapy (RT) apparatus 16, such as a linear accelerator (LINAC). The RT apparatus 16 delivers one or more beams of therapeutic radiation to the patient in accordance with a RT plan developed using the density map 9. The therapeutic radiation may be an accelerated beam of electrons, protons, or so forth. During the radiation therapy, ultrasound images 19 of a patient are taken using an ultrasound imaging device or system 18. The ultrasound images 19 may be either two-dimensional or three-dimensional, and are acquired rapidly enough to provide (approximately) real-time information about the geometry of the thoracic diaphragm, e.g. acquired every 0.5 seconds or faster in some embodiments. As the ultrasound images 19 acquired by the therapy-phase ultrasound instrument 18 are to be correlated with the simulation ultrasound images $^{sim}US(i)$ 12, the probe position and the ultrasound device 18 should be chosen to produce ultrasound images 19 of the same orientation and which are comparable with the simulation phase ultrasound images $^{sim}US(i)$ 12. The ultrasound instrument 10 used to acquire the simulation ultrasound images 12 and the treatment ultrasound instrument 18 used during radiation therapy delivery can optionally be the same instrument, although this is sometimes impractical since the radiation therapy planning may be performed in a different room (or even a different building) from where the radiation therapy treatment delivery is performed.

In operation 20, information is compared and correlated between the simulation and treatment phases. To achieve this, during the treatment phase while therapeutic radiation is being delivered to the patient by the RT apparatus 16, real-time ultrasound (US) images/volumes 19 ($^{Tx}US(t)$, where t represents time, and the superscript $T_x$ denotes a treatment phase ultrasound image) are acquired using the ultrasound imaging system 18 and are compared to simulation-day US images/volumes ($^{sim}US_i$, where the superscript sim denotes a simulation phase ultrasound image). Various similarity metrics such as mutual information, normalized cross correlation, sum of squared differences or distance between the diaphragms segmented in the US images/volume can be used to quantitatively compare the US images/volumes. For each real-time US image/volume 19, a closest simulation phase US image/volume 12 may be found and used to find the positon of the target (e.g. lung tumor) using the equation:

$$i^* = \arg\max_i(SIM(^{sim}US_i, {}^{Tx}US(t)))$$

where SIM( ) denotes a similarity measurement function between the two US images/volumes.

This produces the i* shown in operation 22, which is the index of the simulation image $^{sim}US_{i^*}$ that most closely matches the treatment image $^{Tx}US(t)$.

Then, in operation 24, an actual position of the lung tumor is determined based on the relationship 14 between malignant tumor position T(i) and simulation ultrasound image US(i). This may be done, for example, using the equation:

$$^{Tx}T(t) = {}^{sim}T_{i^*}$$

where $^{sim}T_{i^*}$ is the malignant tumor position for index i* obtained from the relationship 14, and $^{Tx}T(t)$ is the tumor position at the time that the image $^{Tx}US(t)$ is acquired. It will be noted that this tumor position 24 is determined without identifying the malignant tumor in the ultrasound image 19 of the thoracic diaphragm. Based on the lung tumor position $^{Tx}T(t)$, radiation delivered by the RT apparatus 16 may be adjusted in operation 26. This adjustment may, for example, include shuttering the therapeutic radiation beam of the RT apparatus 16 for a time interval during which the tumor has moved out of its target position due to respiration, or may include operating the RT apparatus 16 to move the therapeutic beam in real-time to track respiration-related motion of the tumor.

Figure 2:
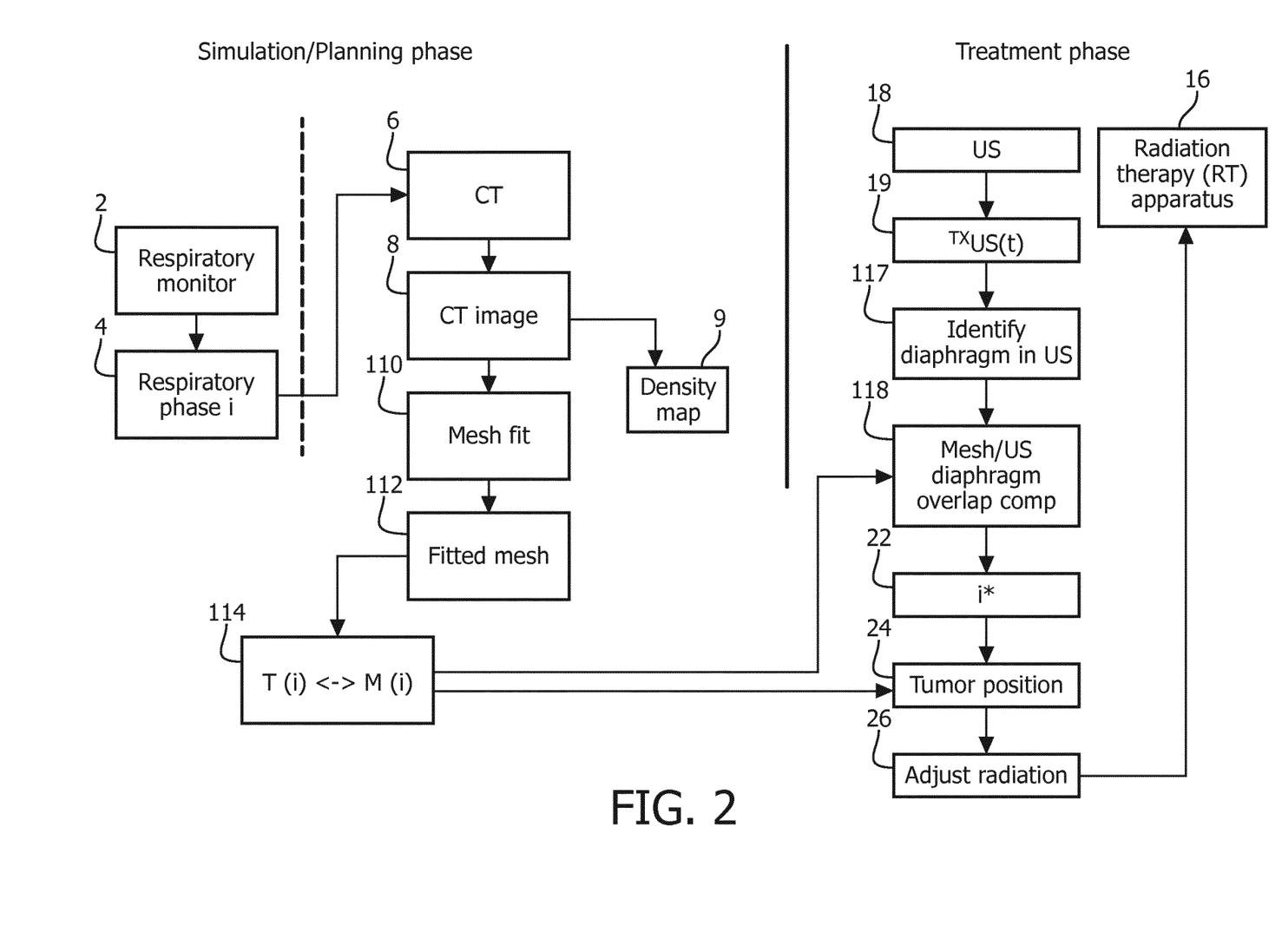
FIG. 2 diagrammatically shows a second preferred embodiment which does not include ultrasound images taken during a simulation phase.

The ultrasound probe 18 used in the ultrasound imaging during the radiation treatment should be spatially co-registered to the linear accelerator (LINAC) coordinate system (or, more generally, to the coordinate system of the radiation therapy apparatus 16 delivering the radiation therapy, which may be a LINAC or some other radiation therapy system depending upon the type of therapeutic radiation); and with the simulation CT coordinate system (i.e. the coordinate system of the CT images 8) and simulation ultrasound images 12. Registration between the CT coordinate system of the CT images 8 and the radiation therapy apparatus 16 can employ any registration technique used in registering the planning coordinate system with the therapy coordinate system, such as using applied fiducial markers, and/or relying on intrinsic anatomical markers, and/or employing a scout scan acquired by an auxiliary imaging system, or so forth. Co-registration of the simulation ultrasound and simulation CT images may be obtained by tracking the ultrasound probe in the CT coordinate system using any tracking technology such as electromagnetic tracking or optical tracking. FIG. 2 diagrammatically shows a second preferred embodiment. In this embodiment, no ultrasound images are acquired during the simulation phase (thus, the simulation-phase ultrasound imaging system 10 is omitted), which simplifies the simulation phase as the radiologist no longer needs to coordinate acquisition of the simulation ultrasound images 12 of the illustrative embodiment of FIG. 1. During the simulation phase, the illustrated CT imaging system 6 (or an MRI or other imaging system capable of imaging both the tumor and the diaphragm) acquires images of the patient which show both the lung tumor and the diaphragm. These images may be, in general, 3-dimensional, although again if used for RT planning then three-dimensional images are usually appropriate in order to generate the density map 9 in three-dimensions for use in the RT simulation/planning. The 4DCT images 8 include both the lung and the thoracic diaphragm. As in the embodiment of FIG. 1, the CT images 8 are used to generate the density map 9. The position T(i) of the lung tumor is obtained by manual, semi-automated, or automated segmentation of the CT image 8. It is also contemplated that the density map and tumor position may be generated using MRI images rather than CT images.

To obtain simulation-phase information about the diaphragm position to coordinate with the tumor position T(i), a mesh fit operation 110 is performed to fit a mesh to the lung in the CT image 8 to generate a fitted mesh M(i) 112 representing the geometry of the diaphragm. Because the lung and diaphragm are closely connected, for improved accuracy the mesh fit operation 110 may fit both the lungs and diaphragm to generate a fitted lung/diagraphm mesh M(i) 112. In either case, a relationship 114 that relates tumor position T(i) obtained from a CT image with the fitted mesh M(i) 112 obtained from the same CT image (that is, a relationship T(i)<->M(i)) then replaces the T(i)<->US(i) relationship 14 of the embodiment of FIG. 1. It will be noted that since the same CT image is used to obtain both T(i) and M(i), the respiratory phase 4 is not used as an index and can be omitted unless (as in illustrative FIG. 2) it is used for respiratory gating of the CT imaging system 6.

With continuing reference to FIG. 2, during the treatment phase, the RT apparatus 16 delivers therapeutic radiation to the patient while ultrasound images of the patient are acquired using the treatment ultrasound device or system 18 as in the embodiment of FIG. 1; this again may be represented by real-time ultrasound images $^{T_x}US(t)$. The ultrasound images are acquired in real-time (e.g. every 0.5 seconds or faster) as the radiation therapy beam is being applied to the patient to perform RT treatment. The ultrasound probe 18 is spatially registered to the linear accelerator (LINAC) coordinate system (or other RT apparatus 16 coordinate system) using a localization technology such as electromagnetic transponders (EM), OSS, optical fiducial markers, or so forth and therefore, the ultrasound probe 18 is also registered to the CT coordinate system. For each ultrasound image/volume acquired by the treatment ultrasound system 18, a best lung/diaphragm mesh is found such that the overlap between the diaphragm part of the lung/diaphragm mesh 112 and the diaphragm image in the ultrasound image/volume is maximized. In one illustrative computational approach, the overlap can be measured using a point-set to image/volume similarity metric on a processed ultrasound images/volumes without segmenting the diaphragm or by measuring the point-set to point-set similarity metric by segmenting the diaphragm in the ultrasound images/volumes. These are merely illustrative examples. The positon of the target can be estimated based on the selected CT volume.

The above described operations are illustrated in FIG. 2 as follows. In operation 117, the diaphragm is identified (e.g. a point set may identify the diaphragm). In operation 118, a diaphragm overlap metric is employed which measures overlap of the CT/MRI diaphragm mesh and the image of the diaphragm in the real-time ultrasound images. In operation 22, i* may be calculated using the equation:

$$i^* = \arg\max_i(L(^{sim}M_i, {^{T_x}US(t)}))$$

Where $^{T_x}US(t)$ are the real-time ultrasound (US) images; t represents time; superscript $T_x$ denotes treatment phase; $^{sim}M_i$ represents the fitted mesh 112; and L measures the similarity between $^{sim}M_i$ and $^{T_x}US(t)$.

Subsequently, in operation 24, the tumor position may be obtained as:

$$^{T_x}T(t) = {^{sim}T_{i^*}}$$

Where $^{sim}T_{i^*}$ is the location of the malignant tumor in the CT image from which the optimally fit mesh $^{sim}M_{i^*}$ was generated. It will be noted that, similarly to the embodiment of FIG. 1, this tumor position 24 is determined without identifying the malignant tumor in the ultrasound image 19 of the thoracic diaphragm.

In a variant embodiment of the illustrative embodiment of FIG. 2, a tracking system to track the probe is not used and the ultrasound (US) probe 18 is not localized respective to the RT system. For this scenario, each real-time US image/volume is registered to all the instances of CT lung mesh based on the diaphragm feature in the US image using any registration method. The mesh with the best registration result (the best similarity metric after registration) can be used to estimate the target positon.

In either the embodiment of FIG. 1 or the embodiment of FIG. 2, the target position 24 may be transferred to the radiation therapy apparatus 16 in order to perform the adjustment 26, for example by moving the radiation beam as the target tumor moves or by stopping delivery of radiation (e.g. shutter off radiation) when the target tumor motion is larger than a pre-specified threshold and/or moves out of a specified spatial range.

Figure 5:
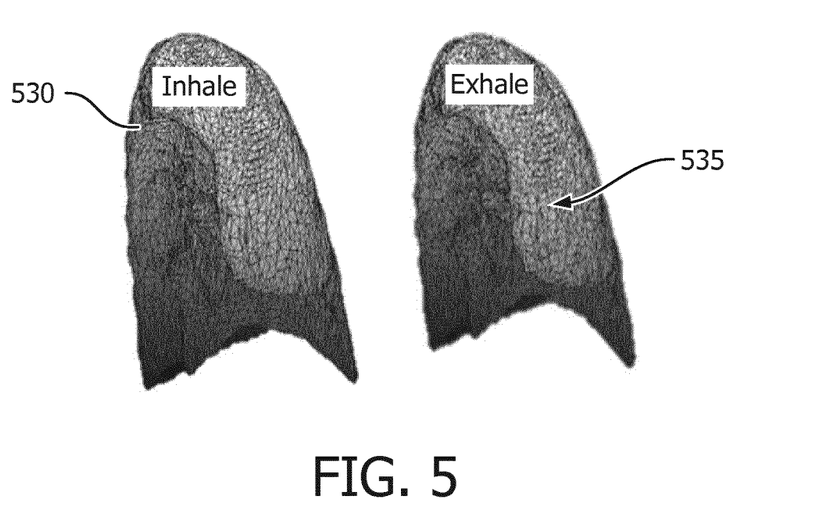
FIG. 5 shows exemplary meshes.

FIG. 5 further illustrates the embodiment of FIG. 2 by showing an illustrative mesh of the lung at full inhale 530, and a mesh of the lung at full exhale 535.

Figure 6:
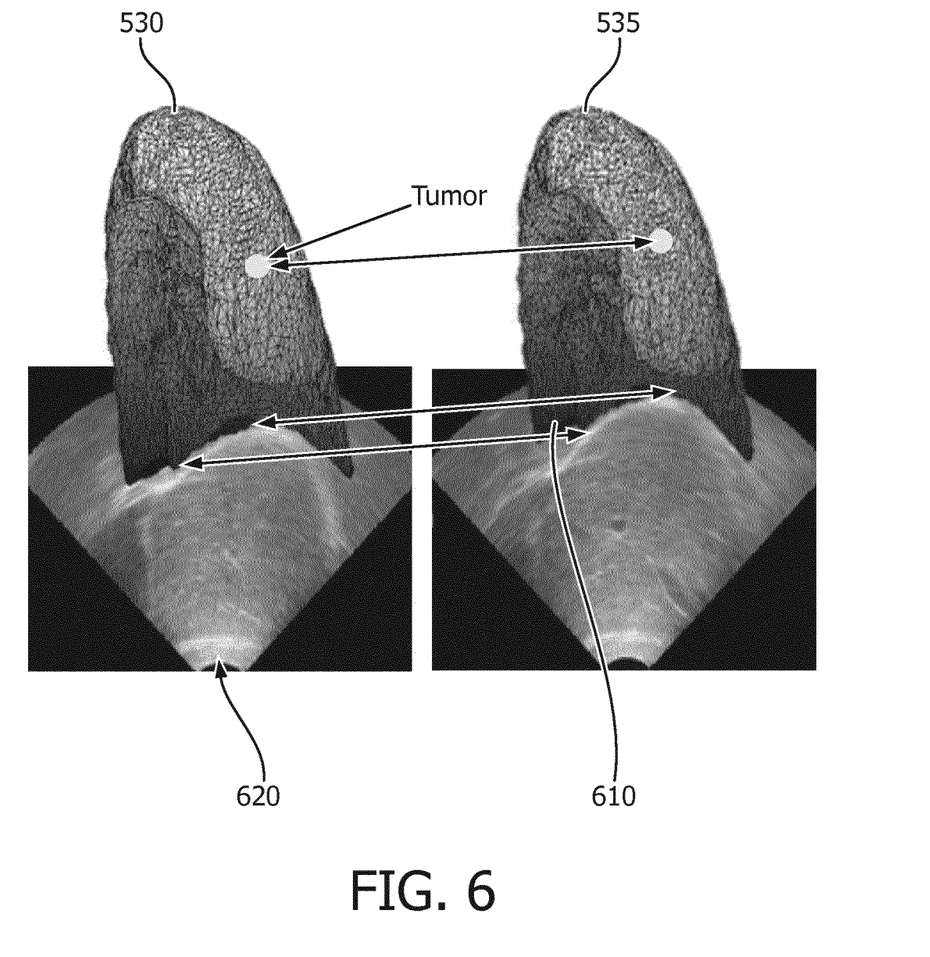
FIG. 6 shows a schematic overlap of US images with meshes.

FIG. 6 illustrates an overlap of US images 620 with the simulation-day lung meshes 530, 535 of FIG. 5, and further including diagrammatic indication of the tumor. The illustrated US images can be used to find the proper breathing phase and estimated the tumor location. Diaphragm 610 in the US image 610 is also labeled.

As a practical matter, US imaging of the left side of the diaphragm may be challenging because the stomach containing gas may interfere with the imaging. Therefore, for tracking a tumor in the left lung, it may be advantageous to also image the diaphragm on the right side. However, US imaging of the left side can also be tried.

Figure 7:
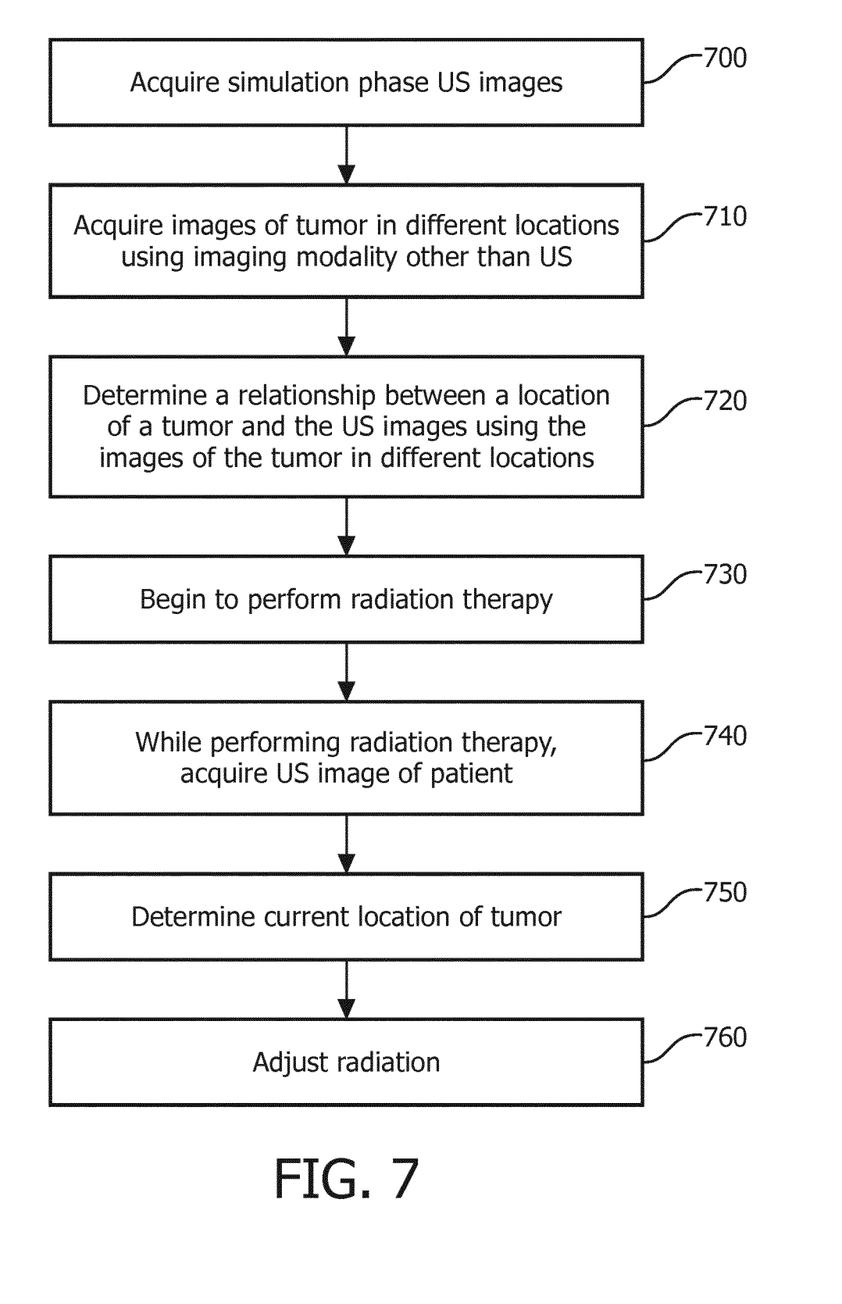
FIG. 7 diagrammatically shows a first preferred embodiment of a method.
Figure 8:
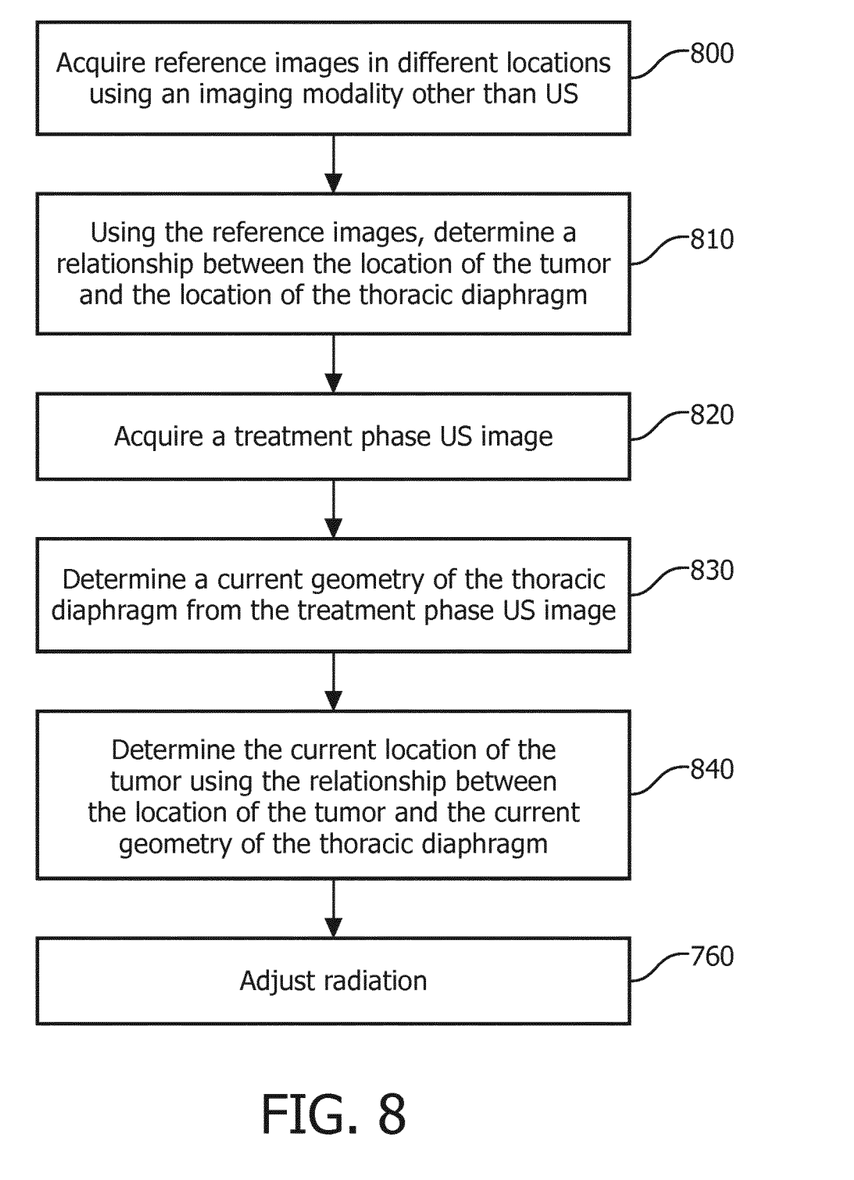
FIG. 8 diagrammatically shows a second preferred embodiment of a method.

FIGS. 7 and 8 illustrate method embodiments. In general, ultrasound imaging to directly measure and track the position of a lung tumor during RT is not practical because of air in the lungs. Accordingly, in some embodiments the tumor-locating methods of FIGS. 7 and 8, while using an ultrasound image, do not include detecting the tumor in the ultrasound image.

FIG. 7 illustrates a preferred embodiment of a first method. With reference thereto, in step 700, simulation phase US images are acquired, which typically do not show the tumor. In step 710, images are acquired of the tumor in different locations using an image modality other than US (e.g. using CT). In step 720, a relationship is determined between the location of a tumor and the US images using the images of the tumor in different locations and a correlation between the US and other-modality images, such as respiratory phase recorded during the imaging. In step 730, radiation therapy begins. In step 740, while performing radiation therapy, US images of the patient are acquired. In step 750, a current location of the tumor is determined using the relationship from step 720. In step 760, radiation is adjusted based on the determined tumor location.

FIG. 8 illustrates a preferred embodiment of a second method, which is suitably used if the simulation-phase ultrasound is unavailable. With reference thereto, in step 800, reference images with the tumor in different locations are acquired using an imaging modality other than US (e.g., using CT). In step 810, using the reference images, a relationship between the location of the tumor and the location of the thoracic diaphragm is determined. In step 820, a treatment phase US image is acquired. In step 830, a current geometry of the thoracic diaphragm is determined from the treatment phase US image. In step 840, a current location of the tumor is determined using the current diaphragm geometry from step 830 and the relationship between tumor location and thoracic diaphragm location from step 810. In step 760, radiation is adjusted based on the determined tumor location.

It will be appreciated that the various data processing disclosed herein, e.g. generating the density map 9 and the relationships 14, 114, the mesh fitting 110 of the embodiment of FIG. 2, the comparison operation 20 or corresponding operations 117, 118 of the embodiment of FIG. 2, and so forth, are suitably performed by an electronic data processing device such as a computer, electronic radiation therapy controller, or so forth, or various combinations thereof It will be further appreciated that these various data processing disclosed herein may be embodied by a non-transitory storage medium storing instructions readable and executable by an electronic data processing device (such as a computer) to perform the disclosed techniques. Such a non-transitory storage medium may comprise a hard drive or other magnetic storage medium, an optical disk or other optical storage medium, a cloud-based storage medium such as a RAID disk array, flash memory or other non-volatile electronic storage medium, or so forth.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. A lung tumor detection device comprising:
an electronic device programmed to:
receive an ultrasound image; and
determine a current location of a lung tumor using the received ultrasound image, without detecting the lung tumor in the received ultrasound image, by:
comparing the ultrasound image only with a plurality of simulation phase ultrasound images to identify a most similar simulation phase ultrasound image; and
determining the current location of the lung tumor using a predetermined relationship assigning a location of the lung tumor to each simulation phase ultrasound image of the plurality of simulation phase ultrasound images.

2. The lung tumor detection device of claim 1 wherein the current location is determined by operations including:
comparing an anatomical feature imaged in the ultrasound image with a plurality of meshes representing the anatomical feature to identify a most similar mesh; and
determining the current location of the lung tumor using a predetermined relationship assigning a location of the lung tumor to each mesh of the plurality of meshes.

3. The lung tumor detection device of claim 2 wherein the anatomical feature is a thoracic diaphragm and the tumor is a lung tumor.

4. The lung tumor detection device of claim 1 further comprising:
an ultrasound device arranged to acquire the ultrasound image that is received by the electronic device.

5. The tumor detection device of claim 1, wherein the electronic device is programmed to determine the current location of the tumor using the received ultrasound image and without detecting the tumor in the received ultrasound image.

6. A lung tumor detection device comprising:
an ultrasound device arranged to acquire a two-dimensional ultrasound image of a thoracic diaphragm using an ultrasound probe positioned inferior with respect to the thoracic diaphragm; and
an electronic data processing device programmed to determine a current location of a lung tumor using the two-dimensional ultrasound image of the thoracic diaphragm and a predetermined relationship based on previously-acquired ultrasound images the predetermined relationship being used for assigning lung tumor locations to a set of simulation phase ultrasound images of the thoracic diaphragm in different geometries, without detecting the lung tumor in the two-dimensional ultrasound image.

7. The lung tumor detection device of claim 6 wherein the correlating comprises:
correlating the determined lung tumor locations with respiratory phase measured during acquisition of the CT images of the lung tumor;
correlating the simulation phase ultrasound images with respiratory phase measured during acquisition of the simulation phase ultrasound images; and
correlating the determined lung tumor locations with the set of simulation phase ultrasound images using the correlated respiratory phases.

8. The lung tumor detection device of claim 6 wherein:
the simulation phase ultrasound images and the images of the lung tumor in different locations are acquired concurrently; and
the relationship is determined by aligning each location of the lung tumor in one of the images of the lung tumor with a concurrently acquired simulation phase ultrasound image.

9. The lung tumor detection device of claim 6 wherein the predetermined relationship assigns lung tumor locations to a set of meshes representing the thoracic diaphragm in different geometries, and the lung tumor detection device further comprises:

a simulation phase electronic data processing device configured to generate the predetermined relationship by operations including:

determining lung tumor locations in computed tomography (CT) images of the lung tumor and the thoracic diaphragm; and generating the meshes by fitting the meshes to the thoracic diaphragm in different geometries in the CT images.

10. The lung tumor detection device of claim 9 wherein the simulation phase electronic data processing device does not process any ultrasound images to generate the predetermined relationship.

11. The lung tumor detection device of claim 10 wherein the simulation phase electronic data processing device is further configured to:

generate a density map of a region including the lung tumor from one or more of the CT images of the lung tumor.

12. The lung tumor detection device of claim 11 wherein the simulation phase electronic data processing device is further configured to:

generate a radiation therapy plan for treating the lung tumor.

13. The lung tumor detection device of claim 6 wherein the predetermined relationship assigns lung tumor locations to a set of simulation phase ultrasound images of the thoracic diaphragm in different geometries, and the electronic data processing device is programmed to determine the current location of the lung tumor by operations including:

calculating a simulation phase ultrasound image index i* according to:

$$i^* = \arg\max_i(SIM(^{sim}US_i, ^{Tx}US(t)))$$

where $^{sim}T_i$ denotes simulation phase ultrasound images and $^{Tx}US(t)$ is the two-dimensional ultrasound image of the thoracic diaphragm; and determining the current location of the lung tumor according to $$^{Tx}T(t) = ^{sim}T_{i^*}$$

where $^{sim}T_{i^*}$ is the location of the lung tumor corresponding to the simulation phase ultrasound image $^{sim}USi^*$ according to the predetermined relationship.

14. The lung tumor detection device of claim 6 wherein the predetermined relationship assigns lung tumor locations to a set of meshes representing the thoracic diaphragm in different geometries, and the electronic data processing device is programmed to determine the current location of the lung tumor by operations including:

calculating an estimated breathing phase i* according to:

$$i^* = \arg\max_i(L(^{sim}M_i, ^{Tx}US(t)))$$

where $^{sim}M_i$ denotes the mesh, $^{Tx}US(t)$ is the two-dimensional ultrasound image of the thoracic diaphragm, and IL measures the similarity between $^{sim}M_i$ and $^{Tx}US(t)$; and calculating the current location of the lung tumor according to:

$$^{Tx}T(t) = ^{sim}T_{i^*}$$

where $^{sim}T_{i^*}$ is the location of the lung tumor corresponding to the mesh $^{sim}Mi^*$ according to the predetermined relationship.

15. The tumor detection device of claim 6, wherein the predetermined relationship assigns tumor locations to a set of simulation phase ultrasound images of the thoracic di a.phragm in different geometries, and the tumor detection device further comprises:

a simulation phase electronic data processing device configured to generate the predetermined relationship by operations including:

determining tumor locations in computed tomography (CT) images of the tumor; and correlating the determined tumor locations with the simulation phase ultrasound images of the thoracic diaphragm.

16. A lung tumor detection method comprising:

acquiring an ultrasound image of a thoracic diaphragm of a patient using an ultrasound probe positioned inferior with respect to the thoracic diaphragm; and determining a current location of a lung tumor of the patient using the acquired ultrasound image and a lung tumor-locating; relationship using a plurality of previously-acquired ultrasound images and without detecting the lung tumor in the acquired ultrasound image.

17. The method of claim 16 further comprising, during a simulation phase preceding the acquiring and the determining, generating the lung tumor-locating relationship by operations including:

(i) acquiring simulation phase ultrasound images of the thoracic diaphragm of the patient, acquiring images of the lung tumor in different locations using an imaging modality other than ultrasound imaging, and determining a relationship between location of the lung tumor and the simulation phase ultrasound images using the images of the lung tumor in different locations acquired during the simulation phase.

18. The method of claim 16 further comprising, during a simulation phase preceding the acquiring and the determining, generating the lung tumor-locating relationship by operations including:

acquiring reference images of the thoracic diaphragm and the lung tumor in different locations using an imaging modality other than ultrasound imaging and determining a relationship between location of the lung tumor and geometry of the thoracic diaphragm using the reference images, wherein the operation of determining the current location of the lung tumor includes determining a current geometry of the thoracic diaphragm from the ultrasound image.

19. The method of claim 16 further comprising:

delivering therapeutic radiation to the patient using a radiation therapy apparatus including adjusting the therapeutic radiation delivered to the patient based on the determined current location of the lung tumor of the patient.

* * * * *